(12) United States Patent
McGuffin

(10) Patent No.: US 8,128,742 B1
(45) Date of Patent: Mar. 6, 2012

(54) METHOD AND APPARATUS FOR MULTI-STAGE AIR TREATMENT SYSTEM

(76) Inventor: Thomas R. McGuffin, Pensacola, FL (US)

( * ) Notice: Subject to any disclaimer, the term of this patent is extended or adjusted under 35 U.S.C. 154(b) by 51 days.

(21) Appl. No.: 12/802,435

(22) Filed: Jun. 8, 2010

(51) Int. Cl.
*B01D 47/02* (2006.01)

(52) U.S. Cl. ............... 96/279; 95/226; 96/333; 96/343; 96/344; 96/348; 96/352; 96/353; 96/371

(58) Field of Classification Search .................. None
See application file for complete search history.

(56) References Cited

U.S. PATENT DOCUMENTS

| | | | | |
|---|---|---|---|---|
| 2,405,494 A * | 8/1946 | Dupuy | | 96/340 |
| 2,409,558 A * | 10/1946 | Gunn | | 95/200 |
| 3,591,947 A * | 7/1971 | Sexton | | 96/259 |
| 3,793,809 A * | 2/1974 | Tomany et al. | | 95/211 |
| 3,815,332 A * | 6/1974 | Bobrowsky et al. | | 96/262 |
| 3,856,487 A | 12/1974 | Perez | | |
| 4,251,485 A * | 2/1981 | Schauer et al. | | 422/168 |
| 4,553,991 A * | 11/1985 | Barsacq | | 96/228 |
| 5,004,486 A * | 4/1991 | Chen | | 96/240 |
| 5,261,933 A | 11/1993 | Greene | | |
| 5,453,107 A * | 9/1995 | Liu | | 96/344 |
| 5,858,072 A * | 1/1999 | Motoda | | 96/332 |
| 5,873,930 A * | 2/1999 | Sanchez | | 96/278 |
| 5,888,277 A * | 3/1999 | Lin | | 96/223 |
| 6,083,307 A | 7/2000 | Dular | | |
| 6,350,302 B1 | 2/2002 | Hallstead, Sr. | | |
| 6,613,130 B2 * | 9/2003 | Givargis | | 95/287 |
| 6,616,733 B1 * | 9/2003 | Pellegrin | | 95/150 |
| 7,246,406 B2 * | 7/2007 | Yarbrough et al. | | 15/353 |
| 7,588,627 B2 | 9/2009 | Kijlstra et al. | | |
| 7,740,691 B2 * | 6/2010 | Cash et al. | | 96/351 |
| 2003/0010214 A1 * | 1/2003 | Naruke | | 96/337 |

* cited by examiner

*Primary Examiner* — Duane Smith
*Assistant Examiner* — Pankti Patel
(74) *Attorney, Agent, or Firm* — George L Williamson

(57) ABSTRACT

Method and apparatus for treating air containing hydrogen sulfide gas, volatile organic compounds, heavy metals and other mercaptans in order to reduce odor and corrosion related to wet wells, dry pits, grease traps and the like. The system comprises a first and second stage air treatment system. A vacuum pump in the primary (stage 2) treatment housing vacuums the contaminated air from the source and pumps the air through a set of diffusers into a treatment fluid wherein the air is then passed through a pair of porous plates and upward through a discharge pump and then into the atmosphere. Prior to treating the air in the primary housing, it is treated in a pretreatment dry air filter wherein the air is inlet into the pretreatment (stage 1) housing and then through a microfilter prior to being passed into the primary housing for further treatment.

6 Claims, 3 Drawing Sheets

METHOD AND APPARATUS FOR MULTI-STAGE AIR TREATMENT SYSTEM

BACKGROUND OF THE INVENTION

1. Field of the Invention

The present invention relates generally to air treatment and, more particularly, is concerned with multi-stage system for removing odor from sewage treatment related devices.

2. Description of the Prior Art

Air treatment devices have been described in the prior art, however, none of the prior art devices disclose the unique features of the present invention. In U.S. Pat. No. 6,616,733 dated Sep. 9, 2003, Pellegrin disclosed a method and means for filtering an air stream with aqueous froth. In U.S. Pat. No. 7,588,627 dated Sep. 15, 2009, Kijlstra, et al., disclosed a process for the removal of hydrogen sulfide and mercaptans from a gas stream. In U.S. Pat. No. 6,350,302 dated Feb. 26, 2002, Hallstead, Sr., disclosed an air filtration system. In U.S. Pat. No. 6,083,307 dated Jul. 4, 2000, Dular disclosed a water filter kit for drywall dust control. In U.S. Pat. No. 5,858,072 dated Jan. 12, 1999, Motoda disclosed a gas suction filtration apparatus. In U.S. Pat. No. 5,261,933 dated Nov. 16, 1993, Greene disclosed a vent gas deodorizing system. In U.S. Pat. No. 3,856,487 dated Dec. 24, 1974, Perez disclosed a gas scrubber. While these air treatment devices may be suitable for the purposes for which they were designed, they would not be as suitable for the purposes of the present invention as hereinafter described.

SUMMARY OF THE PRESENT INVENTION

The present invention discloses a method and apparatus for treating air containing hydrogen sulfide gas, volatile organic compounds, heavy metals and other mercaptans in order to reduce odor and corrosion related to wet wells, dry pits, grease traps and the like. The present invention comprises a first and second stage air treatment system. A vacuum pump in the primary (stage 2) treatment housing vacuums the contaminated air from the source and pumps the air through a set of diffusers into a treatment fluid wherein the air is then passed through a pair of porous plates and upward through a discharge pump and then into the atmosphere. Prior to treating the air in the primary housing, it is treated in a pretreatment dry air filter wherein the air is inlet into the pretreatment (stage 1) housing and then through a microfilter prior to being passed into the primary housing for further treatment.

An object of the present invention is to remove undesirable compounds from the air of wet wells, dry pits, grease traps and the like. A further object of the present invention is to reduce the odor of the air treatment stream. A further object of the present invention is to provide a non-toxic discharge comprising treated air. A further object of the present invention is to provide a means for air treatment which can be easily operated by a user. A further object of the present invention is to provide an air treatment system which can be relatively inexpensively manufactured.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
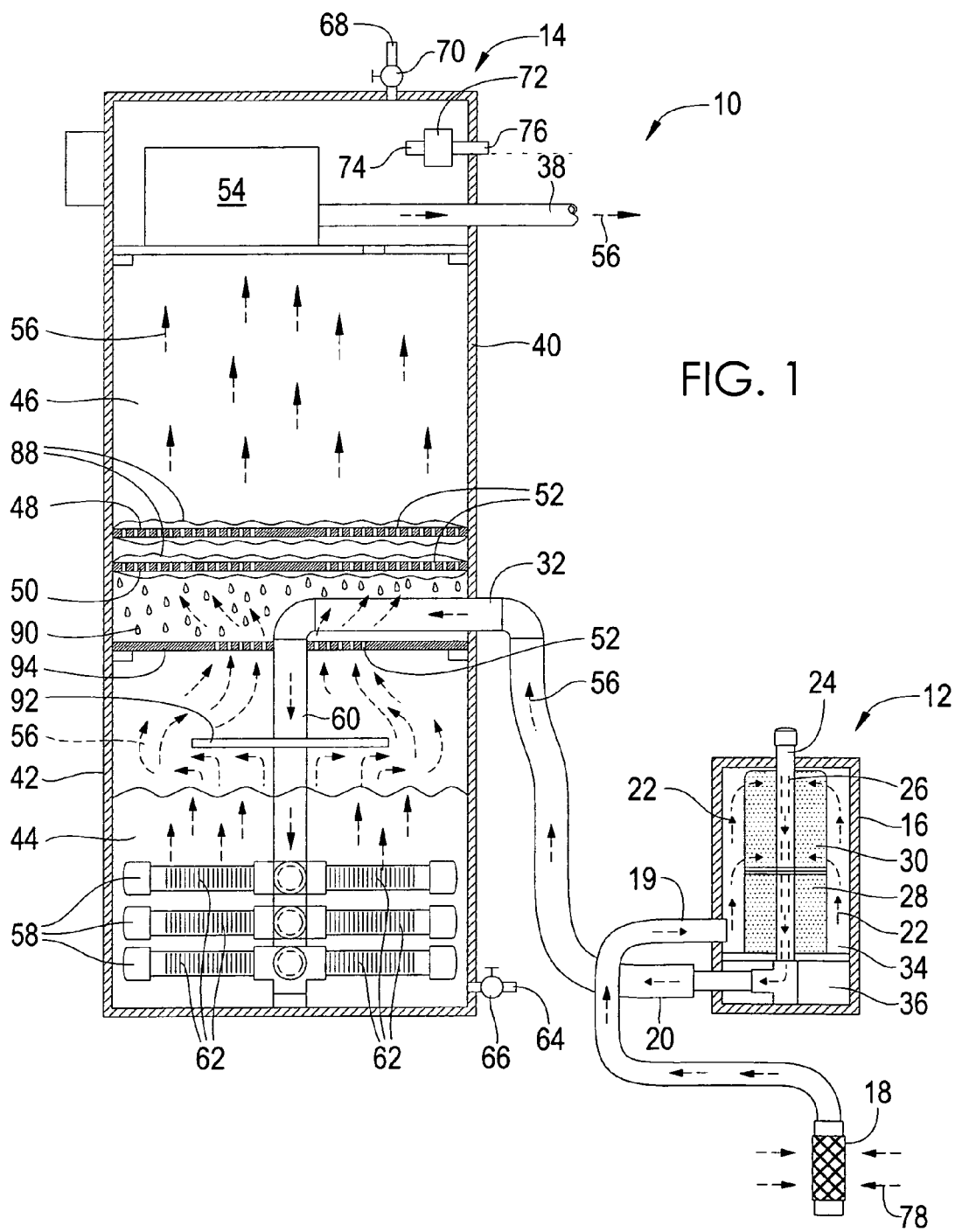
FIG. 1 is a cross sectional view of the present invention.

With regard to reference numerals used, the following numbering is used throughout the drawings.

| | |
|---|---|
| 10 | present invention |
| 12 | stage 1 filter |
| 14 | stage 2 filter |
| 16 | enclosure |
| 18 | inlet nozzle |
| 19 | inlet |
| 20 | outlet |
| 22 | direction arrow |
| 24 | discharge pipe |
| 26 | slot |
| 28 | microfilter |
| 30 | microfilter |
| 32 | inlet |
| 34 | compartment |
| 36 | compartment |
| 38 | outlet |
| 40 | enclosure |
| 42 | lower compartment |
| 44 | treatment fluid |
| 46 | upper compartment |
| 48 | plate |
| 50 | plate |
| 52 | slots |
| 54 | vacuum motor |
| 56 | direction arrows |
| 58 | air diffuser |
| 60 | distribution pipe |
| 62 | diffuser slots |
| 64 | drain pipe |
| 66 | control valve |
| 68 | air vent |
| 70 | control valve |
| 72 | vacuum relief valve |
| 74 | inlet |
| 76 | outlet |
| 78 | arrows |
| 80 | ground |
| 82 | wet well |
| 84 | cover |
| 86 | septic fluid |
| 88 | froth |
| 90 | drop |
| 92 | deflector plate |
| 94 | plate |
| 96 | aperture |

DETAILED DESCRIPTION OF THE PREFERRED EMBODIMENT

Figure 2:
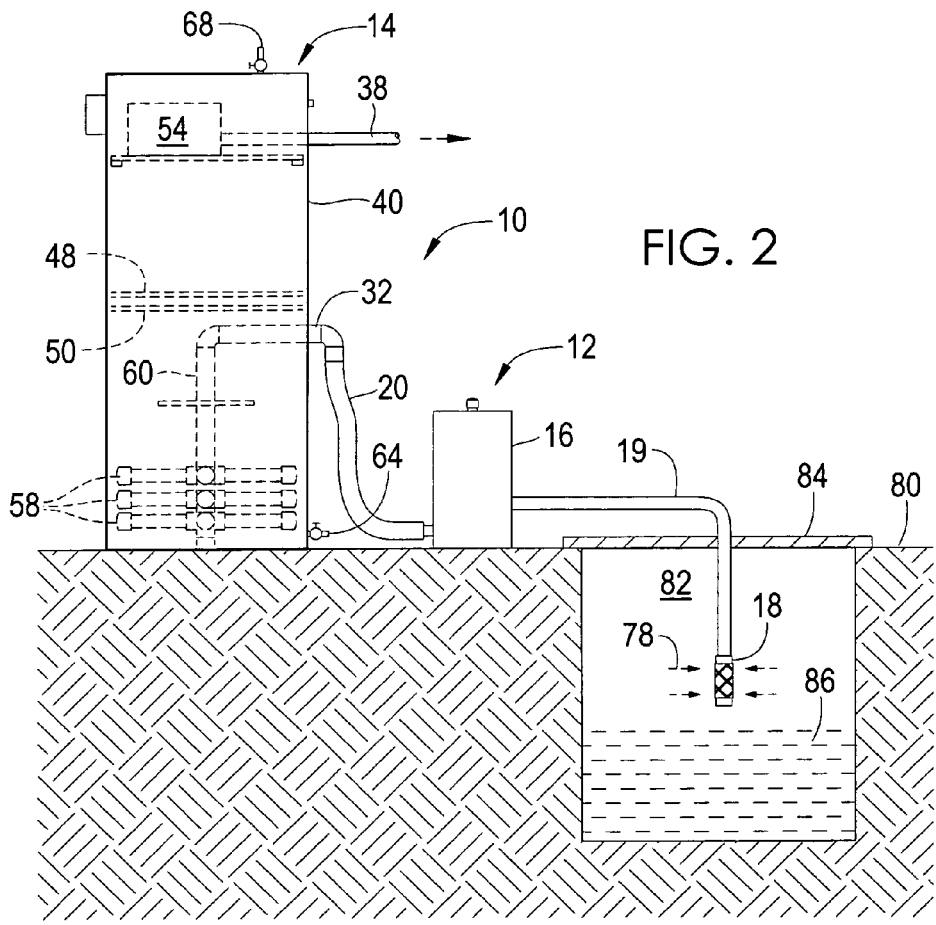
FIG. 2 is an environmental view of the present invention.
Figure 3:
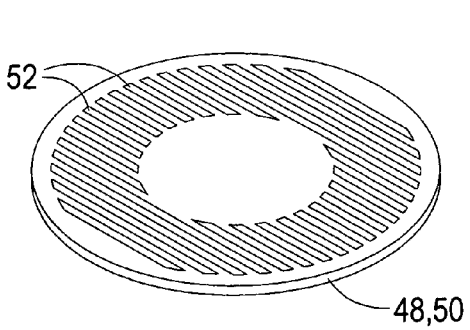
FIG. 3 is a perspective view of a portion of the present invention.
Figure 5:
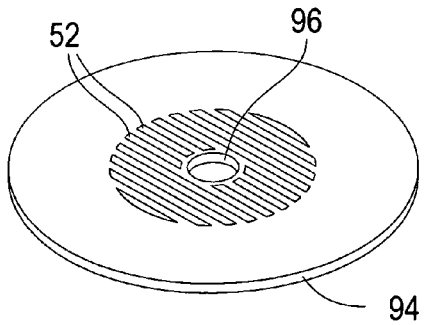
FIG. 5 is a perspective view of a portion of the present invention.
Figure 4:
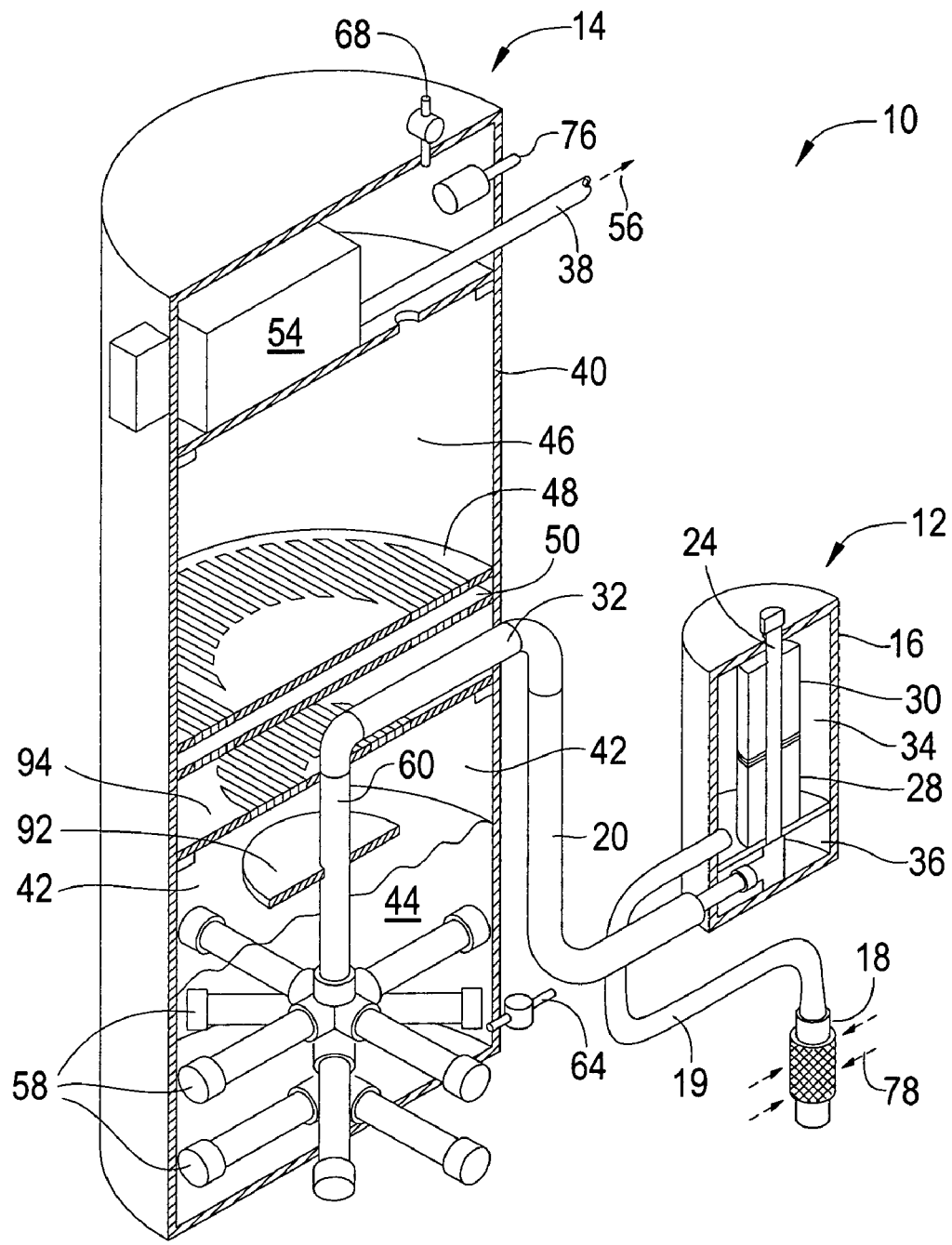
FIG. 4 is a perspective view with cut-away portions of the present invention.

The following discussion describes in detail at least one embodiment of the present invention. This discussion should not be construed, however, as limiting the present invention to the particular embodiments described herein since practitioners skilled in the art will recognize numerous other embodiments as well. For a definition of the complete scope of the invention the reader is directed to the appended claims. FIGS. 1-5 illustrate the present invention wherein a method and apparatus for treating air is disclosed.

Turning to FIGS. 1-5, therein is shown the present invention being generally shown at 10 comprising a Stage 1 dry filtration system 12 and a Stage 2 wet filtration system 14. The Stage 1 filtration system 12 comprises an enclosure or housing 16 having an air inlet nozzle 18 leading into an inlet conduit 19 and an outlet 20 wherein the inner air circulation pattern is shown at arrows 22 and having a first micro air filter 28 and a second micro air filter 30 internal housing 16 so that air passes through the microfilter 28, 30 and then out a vertically disposed central discharge pipe 24 comprising a centrally disposed slotted air conveyance pipe 24 having a plurality of entry slots 26 therein and then into the outlet conduit 20 of the enclosure 16 and into the inlet conduit 32 of the Stage 2 filtration system 14. Arrows 78 illustrate the contaminated airstream containing odorous vapors entering inlet 18. Note that the Stage 1 filter has a first upper compartment 34 containing the microfilter 28, 30 and a second lower compartment 36 containing the outlet 20 so that the two compartments are kept separate from each other in order to improve sanitary conditions. The Stage 2 filter system has an inlet 32 along with an outlet conduit 38 comprising an enclosure or housing 40 having a lower compartment 42 containing a treatment fluid 44 therein and an upper compartment 46 containing first plate 48 and second plate 50 each having a plurality of holes/slots 52 therein, wherein the slots are oriented toward the outer portion of the plates 48, 50 with the center portion being solid, wherein a vacuum blower motor 54 provides means for inducing air flow through the Stage 1 and 2 systems and then out an outlet pipe 38 wherein a plurality of arrows 56 show the air flow through the Stage 2 filter system. Also shown is a solid deflector plate 92 which routes airflow outwardly and then immediately above plate 92 is plate 94 having a plurality of slots 52 disposed toward its center portion and being solid toward its outer portion. The unique orientation and arrangement of slots and solid portions of plates 48, 50, 92 and 94 create a winding path for the airflow which assures complete mixing, volitization of fluid in the airstream, an effectively dry airstream at outlet 38, and increases residence time of housing 40. Other features of the Stage 2 system include a stacked plurality of inner diffusers 58 having a central air distribution pipe or conduit 60 wherein the air passes through the diffusers and out a plurality of slots 62 into the treatment fluid 44, through the plates 50, through the upper compartment 46, through the motor driven vacuum pump 54 and then out the outlet pipe 38. Also shown is a drain outlet 64 having a control valve 66 thereon along with an air vent 68 having a control valve 70 thereon and a vacuum relief valve 72 in order to prevent the housing 40 from collapsing in the event the inlet pipe 32 becomes clogged. The vacuum relief valve has an inlet 74 and an outlet 76.

Regarding plate 92, this is a solid plate designed to deflect the airflow and fluid outwardly and away from the center of the tank 40. There are no holes or slots in this plate. When the air is released from fluid 44 it cause a bubbling action and plate 92 prevents it from hitting the next full plate 94 with the central air slots 52. Plate 94 also has an aperture 96 in its center to accommodate pipe 60. A purpose of plate 92 is to prevent excessive bubble build up in the lower portion of the tank 40.

FIG. 2 also shows an exemplary under the ground 80 wet well 82 with cover 84 containing a septic fluid 86 which emits sewage odors or the like. An inlet nozzle 18 is attached to one end of a non-corrosive EDPM hose 19 and inserted into the contaminated air space 82 where it draws the toxic air outwardly as a part of the airstream. The other end of the hose leads into the Stage 1 filter. A micro diffuser 58 is located in the lower compartment 42 of the tank 40. This micro diffuser 58 is submerged in a concentrated organic solution 44 used to neutralize and remove volatile organic compounds, hydrogen sulfide gas, all other mercaptans, and heavy metals upon contact.

Regarding the diffusers 58, one diffuser will lay flat on the bottom of the tank 40 and will contain air discharge slot openings 62 of 0.006 inch (all measurements are in inches) and the 2nd one will contain air slots opening of 0.004 and the top diffuser will have air slot openings of 0.002. These diffusers are located about 1 inch apart. This will provide a Multi Stage Micro Diffuser 58 that is critical in breaking down and separating the various sewer gases. When these gases are exposed to a vacuum, (negative pressure) they are easily separated due to their various densities, making their molecular structure accessible for our chemical solution to penetrate and destroy the toxic sewer gases. There is a unique chemical reaction that takes place when you combine the specific gravity of the treatment fluid and the vacuum/negative pressure environment that is created in the gas extractor. Plates 48, 50 are located 4 inches apart and each plate will contain air slot openings 52 of 0.002-0.004. This will allow a retention time of 0.75 seconds required before the treated gases are released either back into the atmosphere or the lift station where they were extracted from originally. Air slot openings 26 (0.003) to the Stage I dry air separator 12 is where the toxic gas separation actually starts. This will provide one long micro 24 diffuser inside the canister 16. Plate 94 and its slots 52 are similar to plates 48, 50.

Also shown is a 2 hp regenerative blower 54 and a vacuum relief valve 72. The vacuum relief valve 72 is a critical component to keep the tank 40 from imploding in the event the air intake/stage 1 dry air filter 12 becomes clogged up.

The treatment fluid 44 is an aqueous solution comprising a clear, colorless organic liquid having a ph of about 10 and a boiling point ranging from 212-370 degrees Fahrenheit.

The present invention 10 is a fully self-contained, non-corrosive, multi-chambered, energy efficient, non-hazardous, organic and all green device created to extract, process instantly upon contact, toxic gases such as hydrogen sulfide, volatile organic compounds (VOC's), heavy metals and all other mercaptans which occur naturally in wet wells 82, dry pits, grease traps and the like. The toxic gases are pulled from the wet well 82, dry pit, or grease trap through specifically designed non-corrosive micro diffusers (Stage 1 and 2 at 12, 14) which help break down the toxic gases.

Immediately above the concentrated solution of treatment fluid 44 are multi layers of slotted plates 48, 52, 94 designed to help remove VOC's and hydrogen sulfide gas. The contaminated air is pulled from the well by placing a vacuum on the tank 40. As the vacuum is created, contaminated air is pulled from the air space of the wet well/dry pit or grease trap 82 through the two micro diffusers (Stage 1 and 2 at 12, 14) and through the concentrated solution of treatment fluid 44 where up to 80% of all the VOC's and hydrogen sulfide gas, other mercaptans and heavy metals are instantly removed. As the toxic air travels through the micro diffuser 58 submerged in the concentrated solution 44 agitation occurs. This agitation causes micro foaming froth 88 to accumulate on the plates 48, 50, 94 of the tank and to drop or drip 90 therefrom. As the vacuum occurs in the tank, this pulls the highly concentrated supercharged foam and froth up onto the plates 48, 50. As the plates 48, 50 become saturated and coated with the supercharged micro-fine bubbles created by the agitation in the bottom 42 of the tank, the remaining VOC's, hydrogen sulfide gas, mercaptans and heavy metals are substantially neutralized and removed as they pass through the saturation chambers. This process is fast and irreversible in the state of the process. Final discharge is substantially clean, organically processed air.

This process of extracting and removing toxic gases instantly and on contact is accomplished by using a unique combination of supercharged, micro-foaming, micro diffusers, fluid pressure in a confined space and a regulated vacuum pressure, simultaneously in a multi chambered air tight tank. This makes the present invention a cost-effective closed loop or open loop odor control and toxic gas removal process for wet wells, dry pits and grease traps.

The present invention reduces hydrogen sulfide gas by up to 95%, reduces odor by up to 95%, is an all organic solution, non-hazardous discharge, reduces B.O.D. and C.O.D., retention time >2 seconds (instantaneous and irreversible), water soluble solution, non-toxic discharge, all green construction, fully self contained, no moving parts, 99% maintenance free, super energy efficient, installs in 5 minutes, no retro fitting required, no wiring required (plug into 120 volt outlet), concentrated solution—non DOT regulated, concentrated solution—ships UPS, concentrated solution lasts 90 to 120 days, and the disposal method is to empty used solution into wet well/dry pit or grease trap.

I claim:

1. An apparatus for removing odor from a contaminated airstream from a wet well, comprising:
   a) a first housing, a first inlet disposed on said first housing for inletting the airstream into said first housing, a first outlet disposed on said first housing for discharging the airstream from said first housing;
   b) a filter disposed in said first housing for filtering the airstream, said filter being a dry filter, wherein said filter is disposed internal said first housing so that the airstream passes through said filter between said first inlet and said first outlet;
   c) a second housing, a second inlet and a second outlet disposed on said second housing, wherein said first outlet is connected to said second inlet so that said second housing receives the airstream from said first housing;
   d) a first and second compartment disposed in said second housing, said second compartment disposed above said first compartment, said second inlet disposed on said first compartment so that the airstream enters said first compartment and said second outlet disposed on said second compartment so that the airstream is discharged from said second compartment;
   e) a treatment fluid for removing odor from the airstream, wherein said treatment fluid is disposed in said first compartment;
   f) a plurality of diffusers disposed under a surface of said treatment fluid, wherein said second inlet connects to said diffusers so that the airstream passes through said diffusers and into said treatment fluid so that odor is removed from the airstream, wherein froth is generated as the airstream passes through said treatment fluid;
   g) at least one plate disposed between said first compartment and said second compartment so that said plate is above said surface of said treatment fluid, said plate having a plurality of holes therein, wherein said froth is captured on said plate so that said froth is removed from the airstream; and,
   h) a vacuum pump disposed in said second housing for vacuuming the airstream through the apparatus so that the airstream is conveyed from said first inlet to said second outlet, wherein odors are substantially removed from the airstream.

2. The apparatus of claim 1, said diffusers having a plurality of air discharge openings therein, wherein said openings range in size from 0.002 inch to 0.006 inch in diameter.

3. The apparatus of claim 1, wherein there are three diffusers disposed in a vertically spaced apart manner so that one is above the other.

4. The apparatus of claim 1, said plate having a plurality of slots therein, wherein said slots range in size from 0.002 inch to 0.004 inch in width.

5. The apparatus of claim 1, wherein said treatment fluid is an organic aqueous solution for removing hydrogen sulfide from the airstream.

6. The apparatus of claim 1, further comprising a first, second and third plate disposed between said first compartment and said second compartment so that said first, second and third plate is above said surface of said treatment fluid, said first plate being a solid plate so as to divert airflow outwardly, said second plate having holes disposed toward its center portion so that its outer portion is solid, and said third plate having holes disposed toward its outer portion so that its center portion is solid, wherein the airstream travels in a winding path as the airstream is conveyed from said first inlet to said second outlet.

* * * * *